United States Patent [19]

Wade

[11] Patent Number: 4,588,091
[45] Date of Patent: May 13, 1986

[54] METHOD AND APPARATUS TO DETERMINE QUALITY OF PARTICULATE MATERIAL

[75] Inventor: Franklin J. Wade, Omaha, Nebr.

[73] Assignee: Intersystems, Inc., Omaha, Nebr.

[21] Appl. No.: 498,915

[22] Filed: May 27, 1983

[51] Int. Cl.$^4$ .................................................. B07C 5/00
[52] U.S. Cl. ..................................... 209/546; 209/680;
209/239; 209/237; 73/432 PS; 73/861.23;
364/555; 364/502; 324/71.1
[58] Field of Search ................. 364/502, 555; 209/551,
209/555, 546, 680, 311, 319, 337, 237, 239;
222/370, 344; 73/433, 432 PS, 861.21, 861.23;
324/71.1

[56] References Cited

U.S. PATENT DOCUMENTS

| | | | |
|---|---|---|---|
| 1,222,919 | 4/1917 | Bennett | 73/433 |
| 1,686,946 | 10/1928 | Ayars | 222/370 |
| 2,343,520 | 3/1944 | Baver et al. | 324/71.1 X |
| 2,782,926 | 2/1957 | Saxe | 209/237 |
| 3,545,281 | 12/1970 | Johnston | 209/237 X |

Primary Examiner—Robert B. Reeves
Assistant Examiner—Glenn B. Foster
Attorney, Agent, or Firm—Bernard Malina

[57] ABSTRACT

An apparatus for the measurement of the quality parameters of granular materials includes a loader assembly which delivers precise volume samples of granular material to a meter assembly which measures the moisture content. The apparatus also includes a sieve assembly which separates the samples into fractions according to kernel size. A scale assembly weighs the fractions and feeds this information to a computer which controls the apparatus and calculates the moisture content, density and percentage of foreign material contained in the granular material.

24 Claims, 10 Drawing Figures

METHOD AND APPARATUS TO DETERMINE QUALITY OF PARTICULATE MATERIAL

FIELD OF THE INVENTION

The invention comprises a method and an apparatus for measurement of the quality parameters of samples of grain, seeds and similar granular bulk materials.

BACKGROUND OF THE INVENTION

In order to efficiently market grain, seeds and similar granular materials, both the quantity and the quality must be determined in accordance with accepted measurement standards. Methods for determining the quantity of these materials are currently automated and are sufficiently accurate. However, the methods currently used for measuring quality are subjective and labor intensive. In addition, inhalation of grain dust results in a threat to the prolonged health of the grain quality inspectors.

The prior art includes attempts to automate various quality tests, however, these attempts have not been successful. One of such attempts to automate the testing of grains is shown in U.S. Pat. No. 3,545,281 issued to John A. Johnston. This apparatus uses a vibrating feeder and a weighing station to supply a preselected weight of sample to a set of separating screens. The separating screens separate the oversize particles and the undersize particles from the normal size range of grain particles. The over or undersized particles are conducted to a fraction weighing station where the over or undersigned particles are weighed and this weight is compared with the weight of the entire sample.

This procedure seriously alters the homogeneity of the diverse particulate materials in the original sample and can thereby introduce errors. Since only a preset amount and not the entire sample can be analyzed at a given time, the mixture of foreign material in the analyzed portion may differ from the remaining unanalyzed portion of the sample. This can lead to an error in the overall evolution of the sample. Another disadvantage of this apparatus is related to the inconvenience of analyzing only samples weighing more than the apparatus' preset amount. Consequently, there is no way of evaluating samples which are smaller than the preset amount and yet may be a sufficiently valid representative sample for the desired test.

SUMMARY OF THE INVENTION

In order to overcome the deficiencies of the prior art there is provided, in accordance with the present invention, a method and an apparatus for measurement of the following quality parameters of granular bulk materials: moisture content, bulk density and percentage of foreign material. Moisture content is evaluated in terms of percent of total weight. Bulk density is evaluated in terms of weight per standard volume container (such as, pounds per bushel or kilograms per liter). Percentage of foreign material is evaluated in terms of percent of the weight of sample removed by a standard sieve. Information on standard sieves and inspection methods is published by the Federal Grain Inspection Service USDA in the *Equipment Handbook* (Instruction 916-6), and Grading Procedures Handbook, Grain Inspection Manual, Book II (Instruction 918-6). The apparatus according to the present invention evaluates three of the four principal factors in grading grains. The fourth factor, damaged kernels as a percent of total weight, still must be evaluated by personal inspection of the kernals.

The method according to the present invention may be utilized to evaluate the three quality factors described above as well as additional quality factors such as protein content when such evaluations are required.

During the operation of the apparatus according to the invention a sample of grain or granular material is collected in a known manner prior to being introduced into the apparatus. Generally, in grain handling facilities grain is sampled mechanically, although manual methods are still used occasionally, particularly as a means to check mechanical samplers. Common mechanical samplers include automatically traversing diverters or "pelicans" in the moving grain stream and hydraulically operated probes lowered into stationary vehicles, such as trucks and rail cars. These samples may be reduced from their original size by mechanical dividers that, in effect, collect sub-samples of the initial samples.

The final samples, or sub-samples, may be delivered to the apparatus by dropping through vertical spouts, conveying through pneumatic tubes with high velocity air, hand-carrying in containers loaded at the collection site, or combinations of these and other methods. Upon delivery, if the samples are larger than a size convenient for handling and analysis, they may be reduced further in size, as described above. A practical size for individual samples is 1000 grams, plus or minus 100 grams. In the apparatus according to the present invention, samples may range from about 300 grams to thousands of grams or more. The apparatus may even be set up to receive sample material continuously, generate intermediary analysis results, and calculate summary analysis results at appropriate times.

The apparatus according to the present invention includes a hopper which feeds the grain samples to a loader assembly. The loader assembly delivers a precise volume sample of grain to a meter which measures moisture content. The apparatus also includes a screen assembly which contains standard sieves as specified by the United States Department of Agriculture. A motor drive is provided for oscillating the sieves in order to separate the grain according to kernel size. Hoppers are located below the sieves in order to separately receive the grain which passes through the sieve and grain which is rejected by the sieve. The two grain fractions are conveyed to separate scales where they are weighed.

The apparatus includes separate sieve assemblies for grains which have different nominal sizes such as corn and soy beans and means are provided for loading the grain being analyzed on to the appropriate sieve assembly.

The loader assembly, meter, screen assembly, hoppers and scales are each connected to a microcomputer which controls the operation of the apparatus, calculates the results of each measurement and communicates the results to an operator display and to a printer. The microcomputer is also connected to an auxiliary controller and to a remote computer which may be used to perform control, inventory and accounting functions for an overall grain processing facility, thereby eliminating a need for manually processing the grain quality information generated by the apparatus.

OBJECTS OF THE INVENTION

It is an object of the invention to provide an apparatus capable of accurate, automatic evaluation of the quality of granular materials.

Another object of the invention is to provide an apparatus capable of analyzing a wide range of sample amounts.

Another object of the invention is to provide an apparatus capable of evaluation and recording of the quality of granular material without a need for manual intervention.

Another object of the invention is to provide an apparatus for determination of the quality of granular material in which the control and calculation functions are performed by a microcomputer.

Another object of the invention is to provide an apparatus for determination of the quality of granular material which is capable of operation in a batch mode for evaluation of individual grain samples and in a stream mode for continuous evaluation of a stream of grain.

Another object of the invention is to provide an apparatus for determination of the quality of granular material which is capable of being connected to an auxilliary controller device.

Another object of the present invention is to provide an apparatus for determination of the quality of granular material which is capable of being connected to a remote computer.

Another object of the present invention is to provide an apparatus for determination of the quality of granular material which is capable of evolution of different granular materials having different nominal sizes.

Another object of the present invention is to provide an apparatus for determination of the quality of granular materials which utilizes samples of predetermined volume.

Still another object of the present invention is to provide a method for determination of the quality of granular materials.

Additional objects and advantages of the invention will become apparent during the course of the following specifications when taken in connection with the accompanying drawings in which:

DETAILED DESCRIPTION OF THE INVENTION

Figure 1:
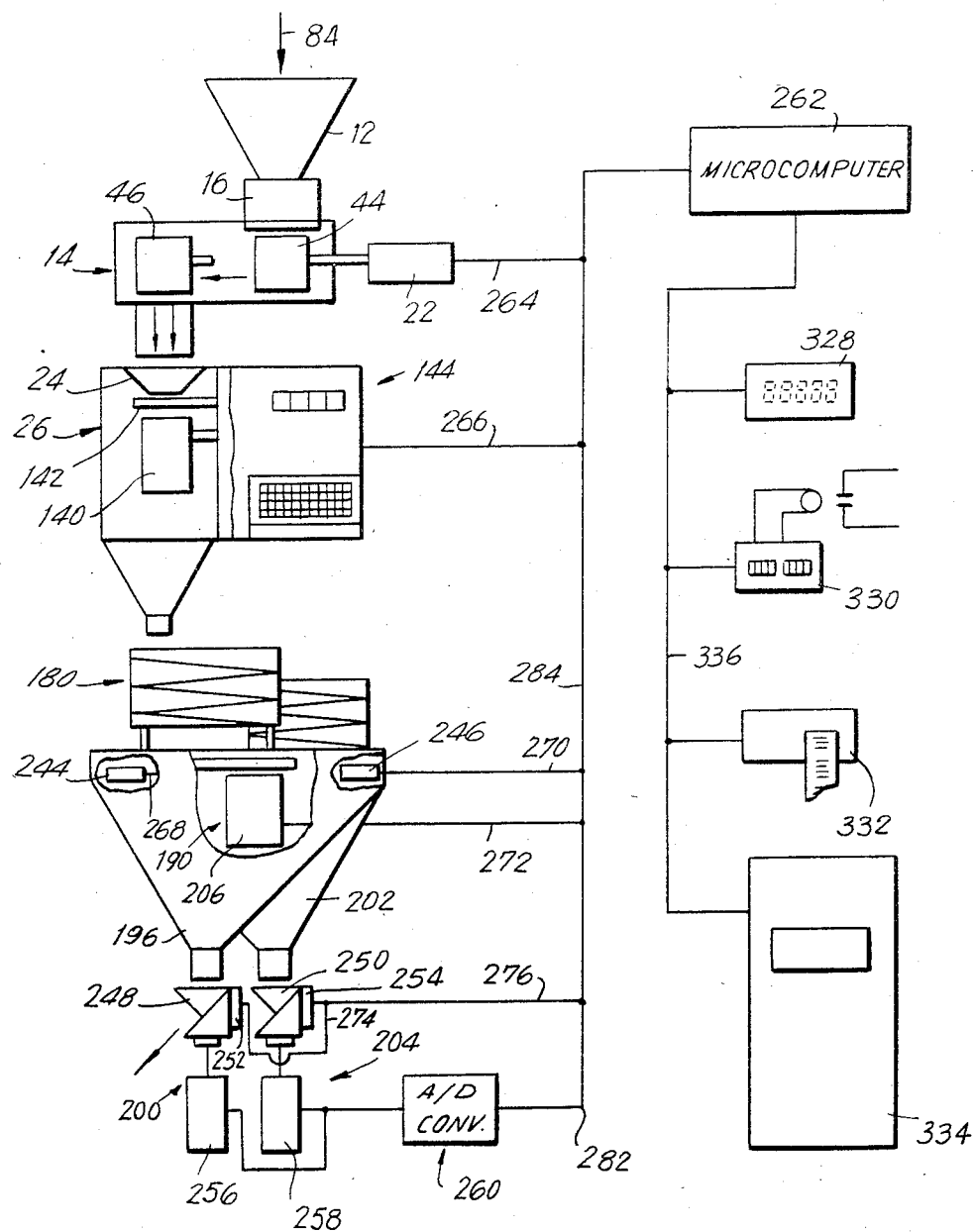
FIG. 1 is a diagrammatic illustration of an apparatus for determination of the quality of granular materials made in accordance with the present invention.
Figure 4:
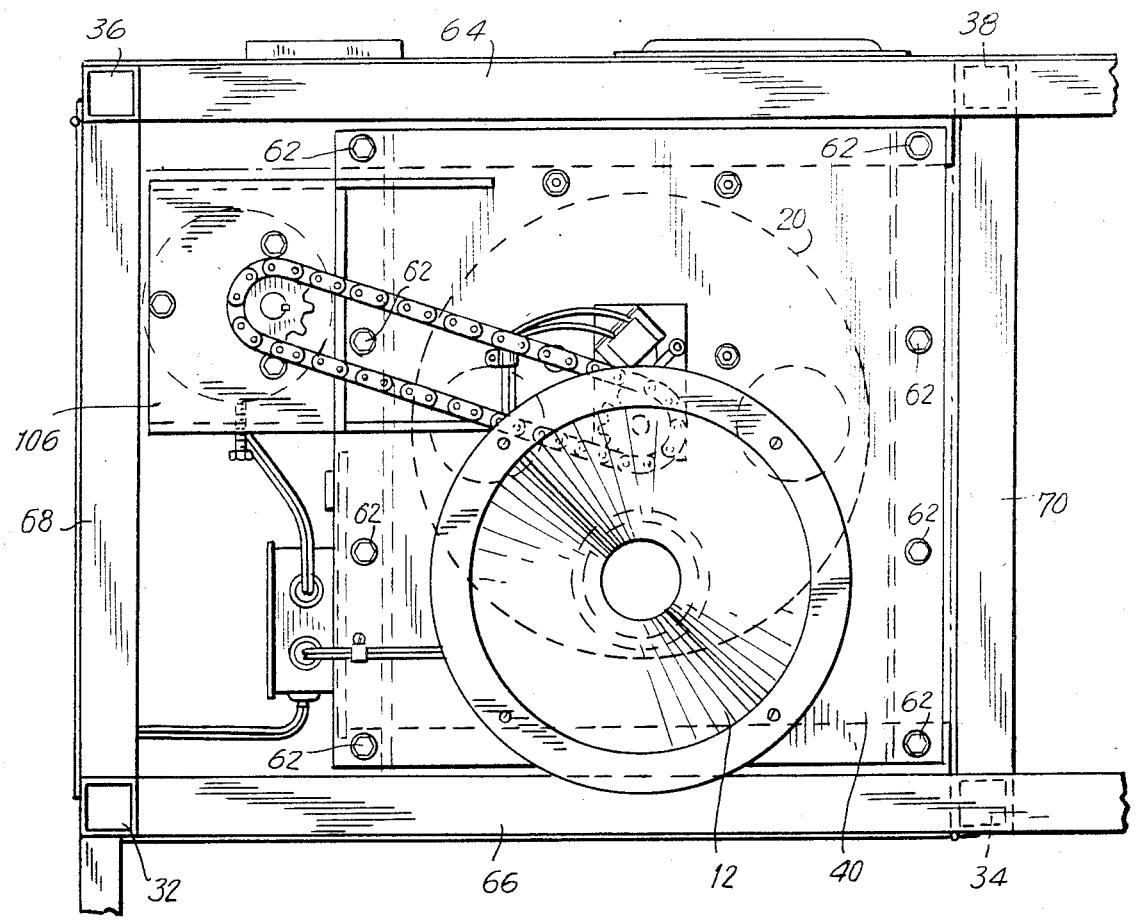
FIG. 4 is a fragmentary top view of the apparatus of FIG. 1 with portions broken away to reveal construction of the loader assembly.
Figure 5:
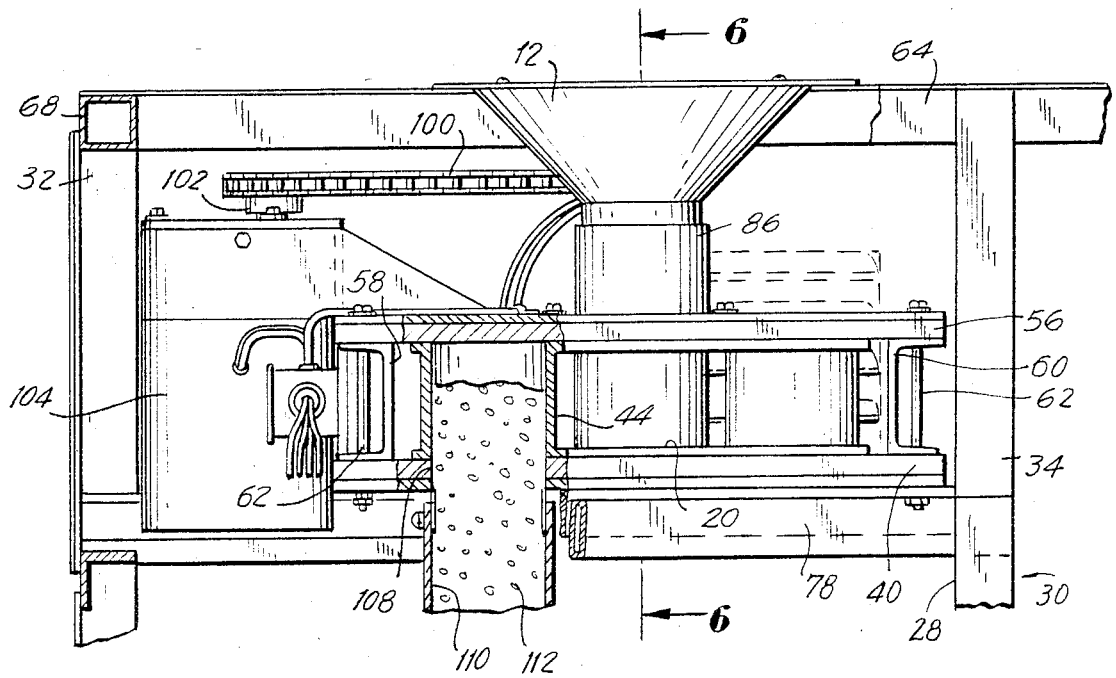
FIG. 5 is a fragmentary front elevation view similar to FIG. 2 with portions broken away to reveal details of internal construction and showing the arrangement of the components of the apparatus during discharge of a sample from the loader assembly.

With reference to FIG. 1, an apparatus 10 for the measurement of the quality of granular materials, according to the present invention, comprises a hopper 12 which feeds grain samples to a loader assembly 14. The loader assembly 14 includes a collar 16 which is located below the hopper 12, and which levels the grain sample. The grain sample is delivered to a container 44, which is located in the loader assembly 14. As is best shown in FIGS. 4, 5 and 6, the container 18 is part of a turntable 20 and the loader assembly 14 includes a drive motor 22 which rotates the turntable 20 so that the container 46 comes into alignment with an inlet hopper 24 at the top of a meter assembly 26.

With reference to FIGS. 2, 3, 4, 5 and 6, the loader assembly 14 is shown mounted on the upper portion 28 of the mainframe of the apparatus 10. The mainframe 30 includes upright members 32, 34, 36, 38 which support cross members 64, 66, 68, 70, 72, 74, 76, 78 and support a mounting plate 40. The mounting plate 40 supports a bearing and shaft assembly 42 on which there is mounted a turntable 20. The turntable 20 includes a pair of cylindrical containers 44, 46, each of which has an open top 48, 50 and an open bottom 52, 54. The turntable 20 is mounted between the mounting plate 40 and an upper plate 56.

The mounting plate 40 and the upper plate 56 are connected by spacers 58, 60 and a plurality of bolts which are designated typically by the reference numeral 62.

Figure 6:
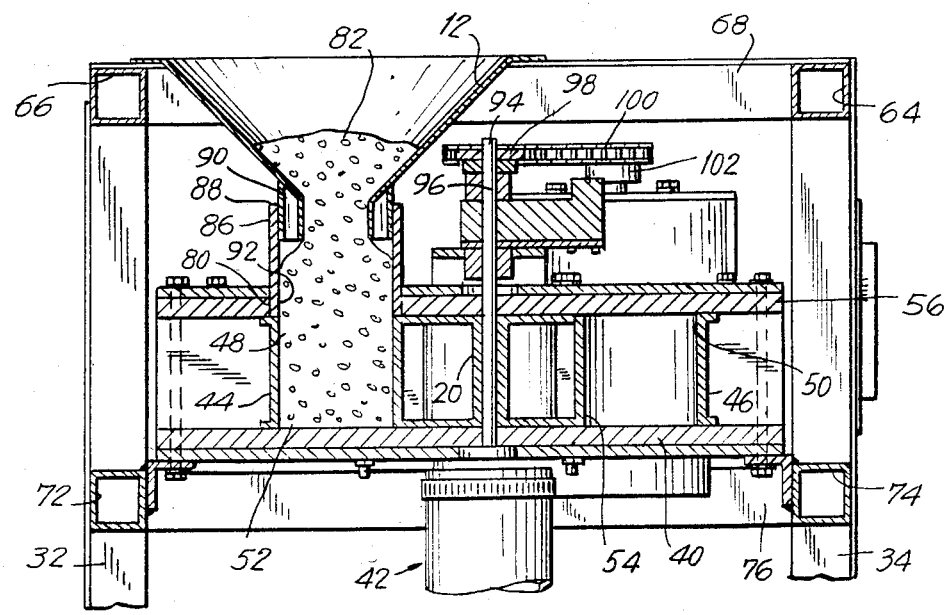
FIG. 6 is a fragmentary sectional view taken along the line 6—6 of FIG. 5 showing the arrangement of the components of the apparatus during filling of the loader assembly.

The upper plate 56 has an aperture 80, located directly below the hopper 12 which permits a sample of grain 82, which has been dropped into the hopper 12, in the direction of the arrow 84 in FIG. 1, to enter the container 44 when the container 44 has been brought into alignment with the aperture 80, as is shown in FIG. 6.

A floating collar 86 is provided which has an upper end 88 which rides on the neck 90 of the hopper 12 and a lower end 92 which rides on the top surface of the turntable 20. The floating collar 86 can move in a vertical direction while being retained by the neck 90 of the hopper 12 and the aperture 80 in the upper plate 56. The floating collar 86 serves to accommodate rotation of the turntable 20 and prevents any spilling of grain.

The upper end 94 of the shaft 96 of the bearing and shaft assembly 42, has a drive sprocket 98 mounted thereon. A drive chain 100 is mounted on the drive sprocket 98 and is also mounted on a drive sprocket 102 which is connected to a drive motor 104 for rotation of the turntable 20. The drive motor 104 is mounted on the upper plate 56 of the loader assembly 14 by means of a bracket 106.

The mounting plate 40 has an aperture 108 directly above the inlet 110 of the meter assembly 26. When the turntable 20 is rotated so that the container 44 is in alignment with the aperture 108, the grain 112 is discharged into the meter assembly 26 as is shown in FIG. 5.

The meter assembly 26 includes a cell 140 which is open at the top. A sufficient sample size of grain causes some kernels to overflow the cell 140 and drop into a tray below. A wire spring arm 142 is provided which pivots across the top of the cell 140 to level the sample. The meter assembly 26 measures the temperature, weight, density and moisture content of the grain in the cell. The moisture content is measured by transmitting a high frequency electric field across the cell. The amount of current, in amperes, is measured and the dielectric constant of the sample is calculated. The temperature, density and dielectric constant of the sample are calculated by an equation using mathematical constants which are stored in a microprocessor, which is not shown but which is located in the meter assembly. The internal construction of the meter assembly is known in the art and need not be described in detail. The meter assembly 26 may be one of any of a number of available systems which measure grain moisture content accurately and provide an external signal corresponding to this measurement. In the present invention a Grain Analysis Computer Model II manufactured by Dickey-John Corporation is used.

Figure 2:
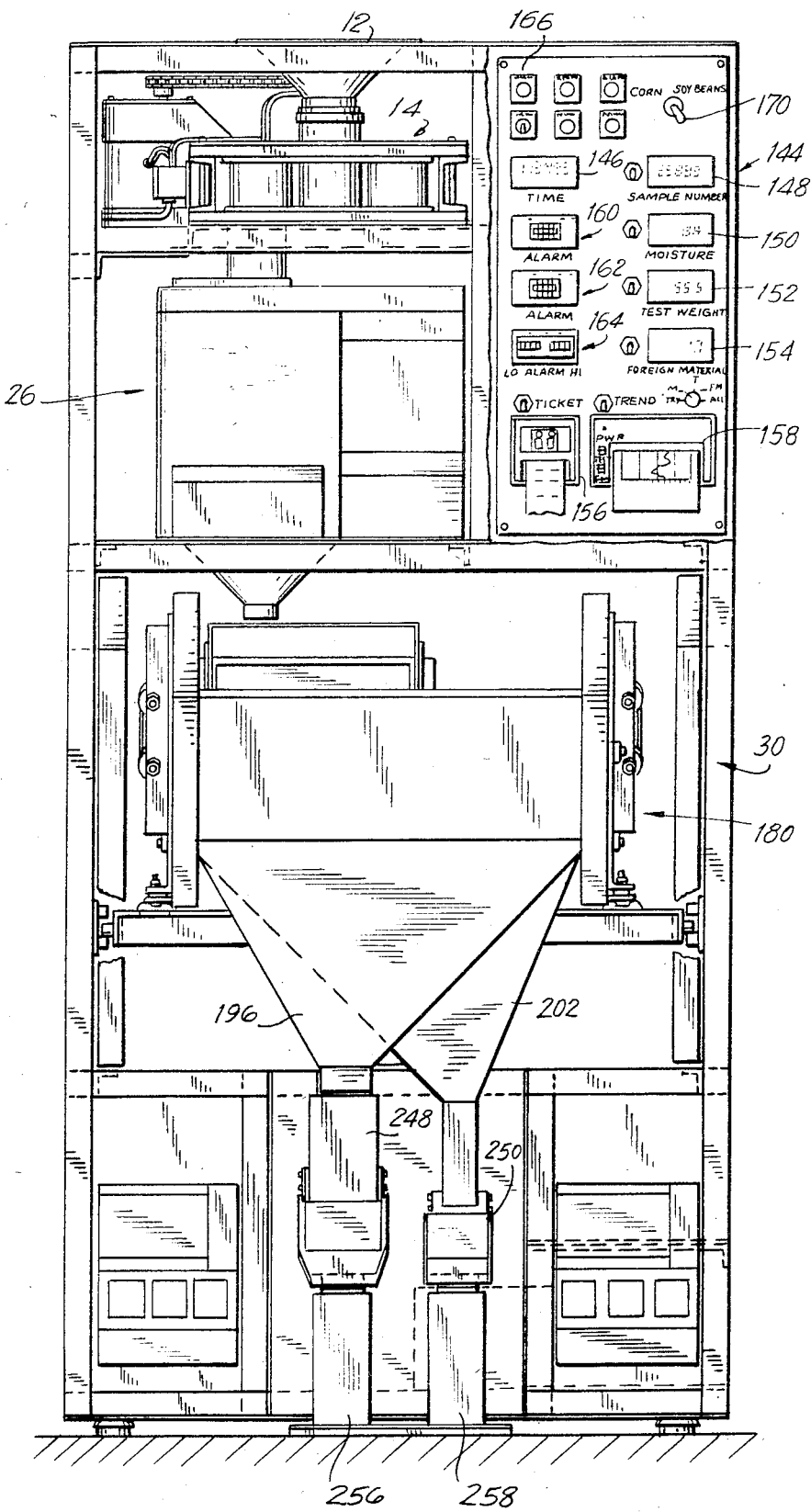
FIG. 2 is a front elevation view of the apparatus of FIG. 1.

The meter assembly 26 is connected electrically to a control panel 144 which is best shown in FIG. 2. The control panel is mounted on the mainframe 30 and includes light emitting diode type displays for digital display of time 146, sample number 148, moisture content 150, test weight 152, and foreign material 154. The control panel 144 also includes an electronic ticket printer 156 for recording the above parameters and a strip chart recorder 158 for recording parameter trends. The control panel 144 includes a bank of alarm indicators 160, 162, 164, a bank of operating switches indicated typically by reference numeral 166, and a selector switch 168 for selection of corn or soybeans. The designation of corn and soybeans has been made for purposes of example only and does not represent a limitation as to the types of grains which can be evaluated by the apparatus 10.

When the measurement performed by the meter assembly 26 has been completed, the sample is dumped out of the cell 140 onto a screen assembly 180.

Figure 3:
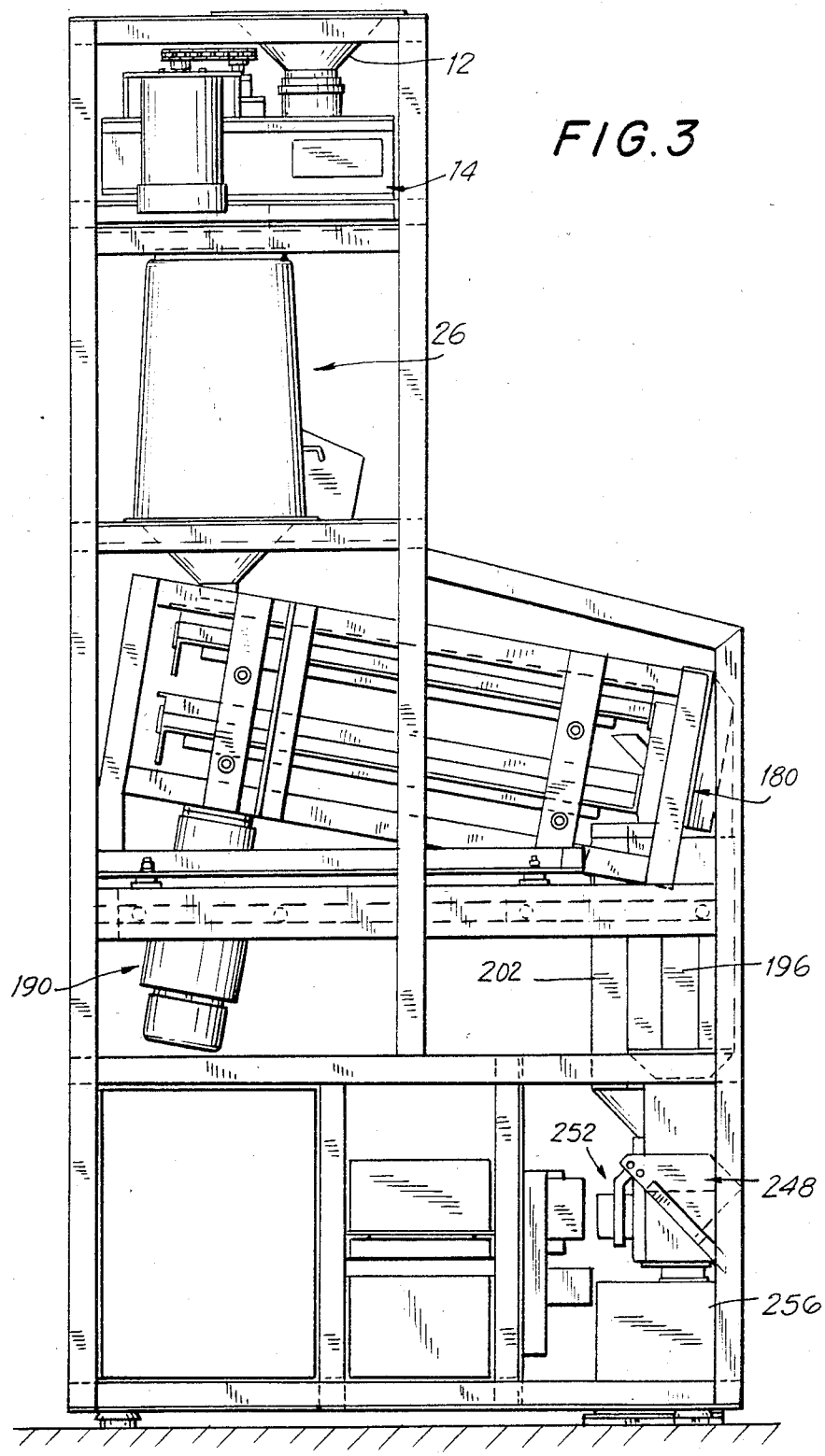
FIG. 3 is a side elevation view of the apparatus of FIG. 1.
Figure 7:
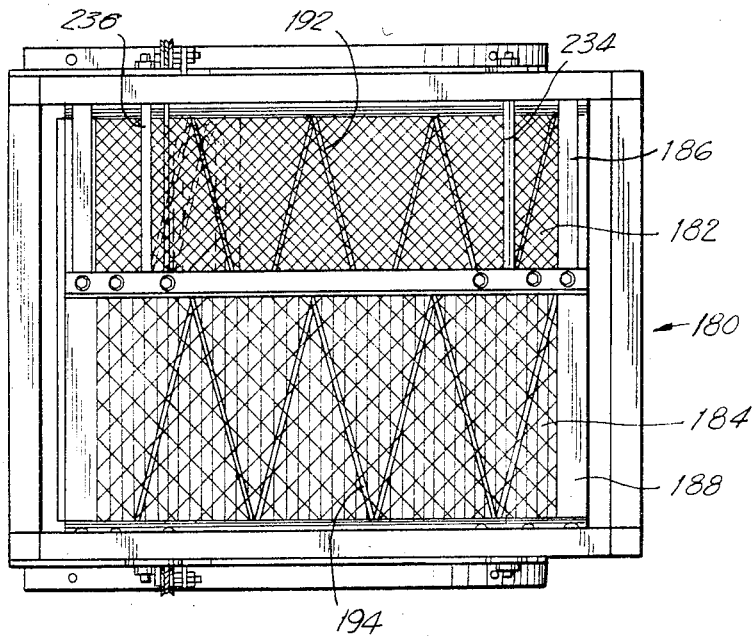
FIG. 7 is a top view of the screen assembly of the apparatus of FIG. 1.
Figure 8:
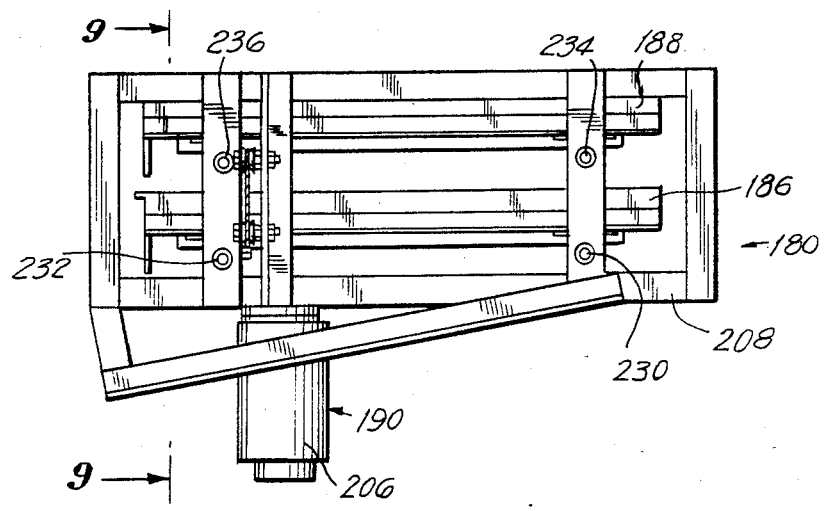
FIG. 8 is a side elevation view of the screen assembly of FIG. 7.
Figure 9:
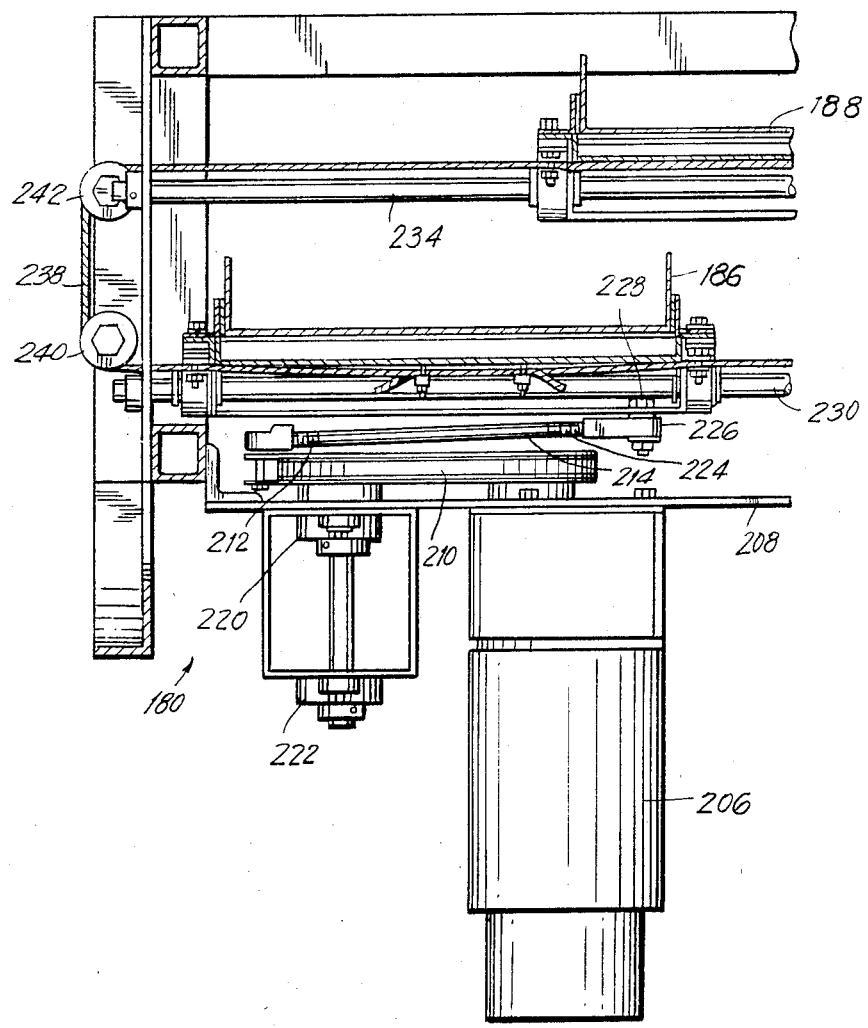
FIG. 9 is a cross sectional view taken along the line 9—9 in FIG. 8.

The screen assembly 180, which is best shown in FIGS. 3, 7, 8 and 9, separates the amount of foreign material and small broken kernel pieces that fall through openings in a sieve. A standard sieve 182, 184 which meets the specifications of the United States Department of Agriculture Federal Grain Inspection Service is provided for each type of grain being evaluated. As is shown in FIGS. 3, 7 and 8, the sieves 182, 184 each form the bottom of a rectangular tray 186, 188 which is inclined slightly with respect to the horizontal. The trays 186, 188 are oscillated sideways by an eccentric drive assembly 190 which is best shown in FIG. 9. The stroke of the trays is in the order of 9 inches and the frequency is in the order of 60 strokes per minutes. A series of metal guides 192, 194 is provided on the sieve surface, as is shown in FIG. 7. The metal guides 192, 194 causes the grain sample to move sideways across the oscillating sieve and down to a hopper 196 which leads to a scale assembly 200. The particles which fall through the sieve are fed via second hopper 202 to a second scale assembly 204.

The eccentric drive assembly 190 includes a drive motor 206 which is mounted on the screen assembly frame 208. The drive motor 206 drives a drive chain 210 on which there is mounted the first end 212 of a threaded rod 214. The drive chain 210 passes over a sprocket wheel 216 which is mounted on a shaft 218 which is rotatably mounted on the screen assembly frame 208 by means of bearings 220, 222. The second end 224 of the threaded rod 214 is attached to a rod end bearing 226 which is connected to the screen tray 186 by means of a bolt 228. The screen tray 186 is guided by a pair of guide rods 230, 232 which are mounted on the screen assembly frame 208.

The screen tray 188 is mounted above the screen tray 186 and is guided by a pair of guide rods 234, 236 which are also mounted on the screen assembly frame 208. The first 186 and second 188 screen trays are connected by an aircraft cable 238 which passes over sheaves 240, 242 so that the first and second trays 184, 186 move in opposite directions.

The apparatus 10 according to the invention includes sensor assemblies 244, 246 which aid the controlling microcomputer 262 to locate the sieves 182, 184 prior to loading and count up to a preset number of strokes, at which time the oscillations are stopped. In the preferred embodiment, two sieves 182, 184, for different grains, such as corn and soybeans, are located one above the other. The sieves 182, 184 oscillate in opposite directions and the momentum of one sieve counteracts the momentum of the other to minimize the overall shaking of the apparatus 10. Either sieve may be loaded by stopping the oscillation as controlled by the microcomputer 262. The microcomputer 262 is connected electrically to the selector switch 170 shown in FIG. 2, thereby allowing an operator to direct the apparatus 10 to properly locate the sieves 182, 184 to load the indicated grain.

The scale assemblies 200, 204 each include a hopper assembly 248, 250, an electric solenoid-operated gate valve 252, 254, a weight sensing transducer 256, 258, and an analog-to-digital converting circuit assembly 260. The gate valves 252, 254 are opened and the transducers 256, 258 are calibrated to read zero grams prior to operation of the apparatus 10. During operation, the transducers 256, 258 each send an electrical signal whose voltage is proportional to the amount of kernels in the scale assembly 200, 204. The analog-to-digital converting circuit assembly 260 converts the analog voltage to a corresponding set of digital signals in a code which can be read by the microcomputer 262.

After the screen trays 186, 188 have stopped oscillating (after 30 to 40 cycles), the entire sample portion is presumed to have been analyzed. The microcomputer 262 reads the weight of the kernels accumulated in scale assembly 200.

The microcomputer 262 also reads the weight accumulated in the scale 204 containing foreign material. The microcomputer 262 determines if all of the original sample has been analyzed using a method which will be presently described. The apparatus 10 begins to load and analyze additional portions of the sample until the sample is completely analyzed or one of the scales' capacities has been reached, at which time the scales' contents will be dumped before analyzing additional portions. Otherwise the microcomputer 262 empties and calibrates both scales 200, 204 when the next sample is initialized or when the "start" button is pressed during operation of the apparatus in a manual mode.

The overall operation of the apparatus is controlled by the microcomputer 262 which reads the various instruments, calculates and communicates the results of the analysis.

The operator switches, and position sensors controls are read by the microcomputer 262 and processed by the microcomputers' program which will be presently described. The microcomputer program generates control signals which are transmitted to operate various instruments, relays, solenoids and indicator lamps.

The microcomputer 262 is connected to the drive motor 22 via the lead 264, to the control panel via the lead 266, to the sensor assemblies via the leads 268, 270, to the drive motor via the lead 272, to the gate valves via the leads 274 and 276, to the transducers via the leads 278, 280, and to the analog-to-digital circuit via the lead 282. The microcomputer 262 is connected to the above leads via the bus 284 which is made up of several parallel interface ports.

Indicator lamps on the front panel 144 indicate whether electrical power is on, when the apparatus 10 is ready to start operation in a manual mode, and when a malfunction has been detected by the microcomputer 262. When the mode selector switch is placed in the off position, or a malfunction occurs, the apparatus 10 is halted. The reset button clears the apparatus 10 of the current sample once it has been halted so that the apparatus 10 may start a new sample. The microcomputer 262 performs both timing and counting operations in order to operate all of the components of the apparatus 10 in proper sequence and also performs a fault detection function to detect the source of malfunction of the apparatus 10.

The microcomputer 262 reads the output of the meter assembly 26 and the scale assemblies 200, 204 and stores these results in separate registers in the microcomputer memory. Calculations are made after the screening of each portion to determine the combined weight of whole kernels and foreign materials in the last portion. Portions weighing less than 75% of the average portion size are considered "remainder portions", that is, the loader container was not filled to capacity; therefore, no sample remains in the loader hopper. A remainder portion less than 25% indicates that the previous portion did not pack correctly in the loader container and that previous portion weight is not included in the average density determination. When a remainder portion is detected the tester stops further loading of sample portions.

Figure 10:
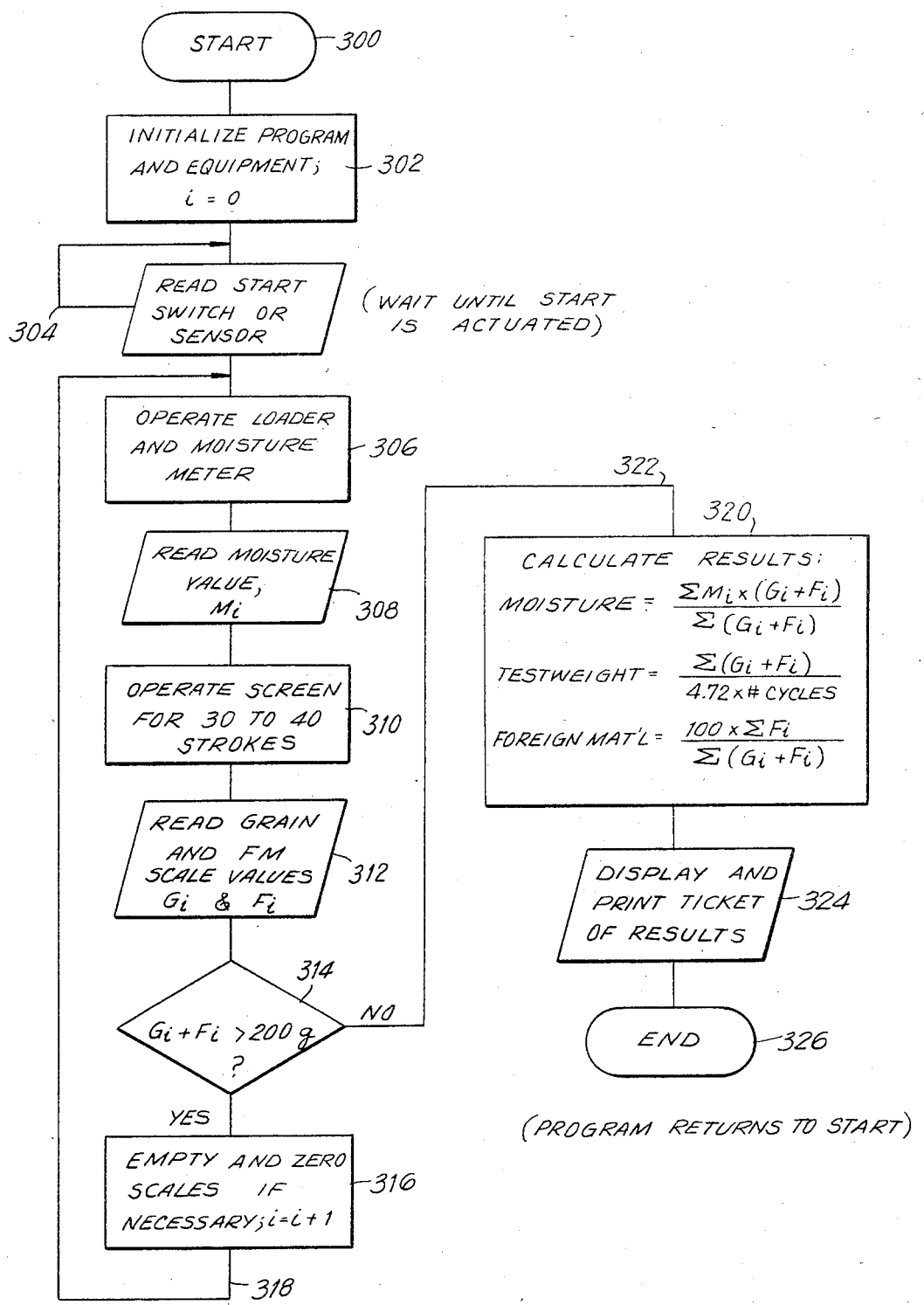
FIG. 10 is a flow chart of the control program of the apparatus of FIG. 1.

The operation of the microcomputer program will be described with reference to the flow chart in FIG. 10. The program start, indicated by the reference numeral 300 leads to an initialization step indicated by the reference numeral 302. The program then reads the start switch or the sensor and waits until start is actuated as indicated by the loop 304. The program operates the loader assembly and the moisture meter and reference numeral 306, and then reads the moisture value, $M_i$, reference numeral 308. The program operates the screen assembly for 30 to 40 strokes, reference numeral 310, and then reads the scale assembly 200, 204 values for weight of grain, $G_i$, and weight of foreign material $F_i$, respectively, reference numeral 312. A typical sampling portion is in excess of 250 grams. Accordingly, in order to determine when the entire sample has been analyzed or check if there is enough material to obtain data, the program checks if the combined value of the grain and the foreign material, $G_i+F_i$, is greater than a preselected amount, e.g. 200 grams, the scales are emptied and zeroed if needed, the program index incremented $i=i+1$, and the program flow returns to the step of operating the loader and the moisture meter assemblies, reference numeral 316 via the loop 318. If $G_i+F_i$ is less than 200 grams, the program performs the following calculation step indicated by reference numeral 320 and line 322:

$$\text{MOISTURE} = \frac{\Sigma M_i \times (G_i + F_i)}{\Sigma(G_i + F_i)}$$

The calculation of MOISTURE includes only those portions for which a valid moisture measurement has been obtained.

$$\text{DENSITY} = \frac{\Sigma(G_i + F_i)}{4.72 \times \text{NUMBER OF CYCLES}}$$

The calculation of DENSITY excludes the weight of remainder and poorly packed portions.

$$\text{FOREIGN MATERIAL} = \frac{100 \times \Sigma F_i}{\Sigma(G_i + F_i)}$$

In the next program step, reference numeral 324, the results are displayed on the control panel and the results are printed on a ticket by the ticket printer 156. The program end, reference numeral 326 then returns the program to start 300.

The above calculations may be further explained as follows:

The moisture content is a weighted average calculation:

MOISTURE CONTENT =

$$\frac{\text{Moisture 1st portion} \times \text{Weight 1st portion}}{\text{Weight all moisture portions}} +$$

$$\frac{\text{Moisture 2nd portion} \times \text{Weight 2nd portion}}{\text{Weight all moisture portions}} + \cdots$$

The calculation of MOISTURE CONTENT includes only those portions for which a valid moisture measurement has been obtained.

The microcomputer calculates the weighted average density of all portions except the remainder portion and the next to last portion if the remainder portion is below 25% of average portion weight. The density is calculated as follows:

$$\text{DENSITY} = \left[ \frac{\text{Weight of 1st portion}}{\text{Volume of Loader Container}} \times \frac{\text{Weight of 1st portion}}{\text{Weight all portions}} \right] + \left[ \frac{\text{Weight of 2nd portion}}{\text{Volume of Loader Container}} \times \frac{\text{Weight of 2nd portion}}{\text{Weight all portions}} \right] + \cdots$$

The calculation of DENSITY excludes the weight of remainder and poorly packed portions.

The density may be converted mathematically to represent the amount of pounds in a bushel (U.S. System) or Kilograms in a liter (Metric SI System). For example, in the invention the volume of the loader cells 44 and 46 are precisely 1/96 of a bushel. Since there are 453.6 grams in one pound, multiplying the number of grams in one cycle of operation of the apparatus by 96/453.6 (or 1/4.72) results in the equivalent number of pounds in a bushel based on that one cycle. To obtain the number of kilograms in a liter, the number of grams in a given cycle is multiplied by 1/367.

The microcomputer calculates the foreign material percentage as follows:

FOREIGN MATERIAL =

$$\frac{100\% \times \text{Weight of all foreign material}}{\text{Weight of all portions}}$$

It should be noted that the percent of foreign material is accurate no matter how much sample is tested. No remainder portions are left in the loader, and no samples need be altered to weigh a predetermined amount. Errors in the moisture and density calculations due to remainder portions are equivalent to those of corresponding manual methods.

The average moisture content, the average density and percent foreign material of the sample are sent by the microcomputer 262 to a remote display 328, an auxilliary controller 330, a remote printer 332, and a remote computer 334, as is shown in FIG. 1. A number representing the identity of the sample is generated by the microcomputer 262 and is sent along with the results and if desired, the hour, date and other data concerning the sample. Communication to the various peripheral equipment described above is made via the Institute of Electrical and Electronic Engineers standard IEEE-488 instrumentation bus 336.

The apparatus 10 according to the present invention is capable of several modes of operation. The first mode as described above covers the analysis of individual samples. A second mode covers the measurement of the quality of samples taken from a long continuous stream. In the second or automatic mode, a mechanical sampler, or a grain weighing system or a sample conveying system which delivers grain samples to the apparatus is monitored to initiate the operation of the apparatus. Each grain sample arriving at the apparatus is analyzed separately, with an intermediary result being generated by the tester. At the end of the stream, several intermediary results are averaged and a composite result is generated. The automatic mode would typically be used to monitor the quality of grain being loaded aboard trains, barges or large bulk carriers.

A variation of the automatic mode of operation includes utilization of the auxilliary control to monitor a specific quality factor such as foreign material and actuate a desired activity within a grain elevator, such as an alarm or a grain cleaning sequence.

Many large grain marketing and processing facilities utilize computer systems to perform control, inventory and accounting functions. The digital output of the apparatus according to the present invention may be transmitted directly to these computers. This capability would allow the facility to operate more efficiently without the previously required paper work. Weight and quality certificates can be consolidated and entry errors can be minimized. A feedback of information to the control and inventory computers would allow rapid response to sudden variations in grain quality during receiving and shipping operations. Grain unloading operations may be streamlined to allow the facility to reject or dispatch each inbound lot to storage at a faster rate, with complete information available on each load before it enters the facility.

While preferred embodiments of the invention have been shown and described herein it is obvious that numerous additions, changes and omissions may be made in such embodiments without departing from the spirit and the scope of the invention.

What is claimed is:

1. An apparatus for the measurement of quality parameters of granular material comprising
   support means,
   loader means, mounted on said support means and capable of receiving said granular material and preparing a volume sample of said granular material,
   metering means, mounted on said support means and capable of receiving said volume sample and measuring the moisture content of said sample,
   screen means mounted on said support means and capable of receiving said sample from said metering means and separating said sample into fractions according to kernel size,
   scale means mounted on said support means and capable of receiving said fractions of granular material and individually weighing said fractions,
   computer means mounted on said support means, and
   electrical connection means connecting said loader means, said metering means, said screen means, said scale means and said computer means for control of the sequence of operation of said loader, metering, screen, scale and computer means and for calculation of moisture content, density and percentage of foreign material contained in said sample.

2. An apparatus according to claim 1 further including hopper means for receiving samples of granular materials and transferring said samples to said loader means.

3. An apparatus according to claim 1 further including ticket printer means for recording said quality parameters calculated by said apparatus.

4. An apparatus according to claim 1 further including continuous strip printer means for continuously recording said quality parameters calculated by said apparatus.

5. An apparatus according to claim 1 in which said electrical connection means is capable of controlling said apparatus in a first mode of operation in which individual samples of granular material are evaluated and a second mode, in which a continuous stream of granular materials are evaluated.

6. An apparatus according to claim 1 in which said screen means includes drive motor means for oscillation of said screen means.

7. An apparatus according to claim 1 in which said screen means includes at least two screens having different mesh sizes and means for selectively placing said granular material on one of said screens.

8. An apparatus according to claim 1 in which said metering means comprises electrical means for measurement of the dielectric constant of said granular material.

9. An apparatus according to claim 2 in which said loader means comprises turntable means, container means mounted on said turntable means, and drive motor means for rotation of said turntable means with said turntable means capable of rotating said container into alignment with said hopper for introduction of granular material into said container means and then out of alignment with said hopper and into alignment with said metering means, thereby delivering to said metering means a precise volume of sample of granular material.

10. An apparatus according to claim 9 further comprising floating collar means disposed to receive granular material from said hopper means and to discharge said granular material into said container means, with said collar capable of motion in a vertical direction.

11. An apparatus according to claim 1 further including an electrical display panel for display of grain quality parameters.

12. An apparatus according to claim 1 further including a remote computer.

13. An apparatus according to claim 1 further including auxiliary controller means.

14. An apparatus according to claim 1 further including auxiliary printer means.

15. An apparatus according to claim 1 in which said scale means includes at least one pair of scales for individually weighing the fraction of the granular sample passed by said screen means and the fraction of the granular sample rejected by said screen means.

16. An apparatus according to claim 1 in which said loader means prepares incremental samples of said granular material and in which said computer means includes means for calculating the moisture content of said granular material by calculating the sum of the moisture content of said incremental samples of granular material multiplied by the weight of each of said incremental samples and then dividing by the weight of all of said incremental samples.

17. An apparatus according to claim 16 in which said computer means further includes means for calculating the moisture content of said granular material only for portions for which a valid moisture measurement has been obtained.

18. An apparatus according to claim 1 in which said loader means prepared incremental samples of said granular material and in which said computer means includes means for calculating the density of said granular material by calculating the weight of said incremental samples of said granular material and dividing each of said incremental samples by the volume of said loader means.

19. An apparatus according to claim 18 in which said computer means further includes means for excluding the weight of poorly packed incremental samples of said granular material from said density calculation.

20. An apparatus according to claim 18 in which said computer means further includes means for excluding the weight of less than full volume samples of said granular material from said density calculation.

21. A method for measurement of the quality factors of granular material comprising the steps of:
Providing sufficient granular material for a plurality of samples each of the same predetermined volume,
Preparing a plurality of samples of said granular material each of the same predetermined volume,
Feeding said samples, one at a time, into a moisture meter,
Feeding said samples, one at a time, into a screen assembly,
Screening said samples into fractions based on particle size,
Weighing each of said fractions,
Calculating the moisture content, the density and the percentage of foreign material of each of said samples.

22. A method for determining the quality factors of granular material according to claim 21 further comprising the steps of:
Displaying the moisture content, the density and the percentages of foreign material of said samples.

23. A method for determining the quality factor of granular material according to claim 21 further comprising the step of:
Recording the moisture content, the density and the percentage of foreign material of said samples.

24. A method for measurement of the quality factors of granular material according to claim 21 further including the step of:
Excluding from said calculation step samples which are less than full volume in size and for which moisture measurement cannot be made.

* * * * *